(12) United States Patent
le Blanc et al.

(10) Patent No.: US 10,524,830 B2
(45) Date of Patent: Jan. 7, 2020

(54) SURGICAL TUNNELER

(71) Applicant: TC1 LLC, St. Paul, MN (US)

(72) Inventors: Pieter W. C. J. le Blanc, Rancho Cordova, CA (US); John Nguyen, San Ramon, CA (US); Keith Kearsley, Burlington, MA (US); Julien Duhamel, Billerica, MA (US)

(73) Assignee: TC1 LLC, St. Paul, MN (US)

( * ) Notice: Subject to any disclaimer, the term of this patent is extended or adjusted under 35 U.S.C. 154(b) by 278 days.

(21) Appl. No.: 15/581,462

(22) Filed: Apr. 28, 2017

(65) Prior Publication Data

US 2017/0224377 A1 Aug. 10, 2017

Related U.S. Application Data

(63) Continuation of application No. 14/135,155, filed on Dec. 19, 2013, now abandoned.

(Continued)

(51) Int. Cl.
*A61B 17/34* (2006.01)
*A61N 1/372* (2006.01)
(Continued)

(52) U.S. Cl.
CPC .......... *A61B 17/3415* (2013.01); *A61B 17/32* (2013.01); *A61B 17/320016* (2013.01); *A61M 1/1086* (2013.01); *A61M 1/122* (2014.02); *A61N 1/372* (2013.01); *A61B 2017/00469* (2013.01); *A61B 2017/320056* (2013.01)

(58) Field of Classification Search
CPC ............ A61B 17/3415; A61B 17/3468; A61B 17/06109; A61B 17/3403; A61B 2017/320052; A61B 2017/320056; A61B 2017/3405; A61B 2017/3407; A61B 2017/3409; A61B 2014/3411; A61B 2017/3425; A61B 2017/3427; A61B 2017/0046; A61B 2017/00464; A61B 2017/00469; A61B 2017/00473; A61B 2017/320044; A61B 2017/00455; A61B 2017/2918; A61B 1/0052; A61M 25/0194; A61M 2025/0197; A61M 2025/09116;

(Continued)

(56) References Cited

U.S. PATENT DOCUMENTS 4,299,228 A 11/1981 Peters
4,509,516 A 4/1985 Richmond
(Continued)

FOREIGN PATENT DOCUMENTS

WO WO 2003/008020 1/2003
WO WO 2006/050191 5/2006

*Primary Examiner* — Katherine H Schwiker
(74) *Attorney, Agent, or Firm* — Squire Patton Boggs (US) LLP

(57) ABSTRACT

A surgical tunneler assembly is used to pass a cable or other elongate member through the skin. A surgical tunneler may include a lance including a first segment, a second end segment, and a connector on each one of the first end segment and the second end segment. A cable adapter includes a lance connection portion and a cable connection portion. The lance connection portion engages and disengages the connectors. The cable connection portion engages and disengages a cable. A handle engages and disengages the lance.

14 Claims, 17 Drawing Sheets

Related U.S. Application Data

(60) Provisional application No. 61/746,441, filed on Dec. 27, 2012.

(51) Int. Cl.
*A61B 17/32* (2006.01)
*A61M 1/12* (2006.01)
*A61M 1/10* (2006.01)
*A61B 17/00* (2006.01)

(58) Field of Classification Search
CPC .............. A61M 25/0136; A61M 1/122; A61M 1/1086; A61N 1/372
See application file for complete search history.

(56) References Cited

U.S. PATENT DOCUMENTS

| | | | |
|---|---|---|---|
| 4,924,851 A | 5/1990 | Ognier et al. | |
| 5,306,240 A | 4/1994 | Berry | |
| 5,555,893 A * | 9/1996 | Hackett | A61M 25/0127 600/585 |
| 5,579,668 A | 12/1996 | Kozak | |
| 5,588,812 A | 12/1996 | Taylor et al. | |
| 5,681,318 A * | 10/1997 | Pennig | A61B 17/72 606/86 R |
| 5,944,732 A | 8/1999 | Raulerson et al. | |
| 6,475,244 B2 | 11/2002 | Herweck et al. | |
| 6,582,439 B1 * | 6/2003 | Sproul | A61B 8/12 606/86 R |
| 6,605,094 B1 | 8/2003 | Mann et al. | |
| 6,911,003 B2 | 6/2005 | Anderson et al. | |
| 6,991,595 B2 | 1/2006 | Burke et al. | |
| 7,048,682 B2 | 5/2006 | Neisz et al. | |
| 7,128,734 B1 | 10/2006 | Wilson et al. | |
| 7,267,645 B2 | 9/2007 | Anderson et al. | |
| 7,578,803 B2 | 8/2009 | Rome et al. | |
| 7,686,760 B2 | 3/2010 | Anderson et al. | |
| 7,740,576 B2 | 6/2010 | Hodroff et al. | |
| 7,798,952 B2 | 9/2010 | Tansley et al. | |
| 7,811,223 B2 | 10/2010 | Hodroff et al. | |
| 7,850,594 B2 | 12/2010 | Sutton et al. | |
| 7,867,161 B2 | 1/2011 | Staskin et al. | |
| 8,043,204 B2 | 10/2011 | Anderson et al. | |
| 8,083,728 B2 | 12/2011 | Rome | |
| 8,088,138 B2 | 1/2012 | Pandey | |
| 8,100,884 B2 | 1/2012 | Schweikert et al. | |
| 8,105,313 B2 | 1/2012 | Schweikert et al. | |
| 8,147,397 B1 * | 4/2012 | Witzmann | A61B 17/062 600/29 |
| 2003/0009854 A1 * | 1/2003 | Shippert | B25G 1/102 16/430 |
| 2003/0045892 A1 | 3/2003 | Kaladelfos | |
| 2004/0106845 A1 | 6/2004 | Anderson et al. | |
| 2005/0090741 A1 * | 4/2005 | Kisen | A61B 17/3403 600/439 |
| 2005/0288762 A1 | 12/2005 | Henderson et al. | |
| 2006/0009783 A1 | 1/2006 | Rome et al. | |
| 2006/0030871 A1 | 2/2006 | Hain et al. | |
| 2006/0084944 A1 | 4/2006 | Ferguson | |
| 2006/0135949 A1 | 6/2006 | Rome et al. | |
| 2007/0118148 A1 * | 5/2007 | Daniele | A61B 17/3468 606/108 |
| 2007/0173879 A1 | 7/2007 | Pandey | |
| 2008/0097409 A1 * | 4/2008 | Stephens | A61B 17/3415 604/533 |
| 2009/0030444 A1 * | 1/2009 | Pandey | A61B 17/32 606/190 |
| 2009/0137944 A1 | 5/2009 | Haarala et al. | |
| 2009/0163770 A1 * | 6/2009 | Torrie | A61B 17/025 600/114 |
| 2010/0063512 A1 | 3/2010 | Braga et al. | |
| 2010/0063513 A1 | 3/2010 | Braga et al. | |
| 2011/0015480 A1 | 1/2011 | Hodroff et al. | |
| 2011/0118766 A1 | 5/2011 | Reichenbach et al. | |
| 2011/0282133 A1 | 11/2011 | Anderson et al. | |
| 2012/0010458 A1 | 1/2012 | Anderson et al. | |
| 2012/0046514 A1 | 2/2012 | Bourque | |
| 2012/0046515 A1 | 2/2012 | Woo et al. | |
| 2012/0059321 A1 | 3/2012 | Hammond et al. | |
| 2012/0083794 A1 | 4/2012 | Martin et al. | |
| 2012/0083826 A1 | 4/2012 | Chao et al. | |
| 2012/0253100 A1 * | 10/2012 | Chisholm | A61B 17/3403 600/8 |

\* cited by examiner

SURGICAL TUNNELER

CROSS-REFERENCE TO RELATED APPLICATION

This application is a continuation of application Ser. No. 14/135,155, filed Dec. 19, 2013, which claims the benefit of U.S. Provisional Application No. 61/746,441, filed Dec. 27, 2012, which applications are incorporated herein by reference in their entirety and for all purposes.

FIELD OF THE INVENTION

This invention relates generally to a surgical tool, more particularly, a surgical tool for placing a cable through the skin.

BACKGROUND OF THE INVENTION

Implantation of various medical devices requires forming a tunnel through the skin or body for placement of a catheter, cable, or other elongate member. For example, a cable must be passed through the skin to connect to many types of implantable devices. The cable may connect the implanted device to an external controller that provides electrical power, data, and/or control signals. Various systems may require tunneling a cable between two or more implanted structures. For example, it may be necessary to connect an implanted electronics housing in one anatomical location to an operative device in another location. In another example, certain medical procedures require placement of a catheter in a patient's body for an extended period of time.

A surgical tool used to pass the electrical cable through the skin is often referred to as a tunneler. Different types of tunnelers are available and suitable to particular methods of tunneling. Certain surgical procedures require a tunneler that can push through tissue in two directions. Such tunnelers are sometimes referred to as bi-directional tunnelers. Tunneler assemblies often are provided as part of a tool set including adaptors, plugs, and caps.

Existing surgical tools often suffer from several drawbacks. In the example of implantation of a left ventricular assist device (LVAD), a surgical team may be called on to tunnel a percutaneous cable between the LVAD and an external controller. Existing tools may require a lance to create a passageway through the skin and another tool to pull the cable through the passageway. Some tools may be designed to form the passageway and pull the cable, but these tools typically still require a cumbersome exchange of adaptors. Additionally, the elongate shape of the lance can make it difficult for a clinician to firmly grasp the tunneler and get sufficient leverage to push through tissue. Some tunnelers are designed with a handle removable from an elongate lance that performs the tunneling. The handle allows the clinician to manipulate the lance in the tissue. If the clinician needs to push the lance completely through the tissue, however, there must be a way to remove the handle. Existing designs lack an easy way to attach the handle to the lance in a robust manner and an easy way to remove the handle. For example, many tools require a user to screw a handle onto the lance, which adds significant time to the procedure. Moreover, when the handle is removed, the clinician lacks any finger holds for the last bit of pushing.

There is a continuing need for an improved tunneler, for example, one that is easy to use and allows for flexibility of use in a variety of tunneling methods. There is a continuing need for a tunneler that decreases the time for surgical procedures. There is a need for a tunneler with improved versatility, control, and ease of use to efficiently create a path through soft tissue. There is a continuing need for a lower cost tunneler useful in a variety of applications. There is a continuing need for a tunneler assembly that overcomes these and other problems.

SUMMARY OF THE INVENTION

Briefly and in general terms, the present invention is directed to a surgical tunneler assembly and surgical implantation kit.

Various aspects of the invention are directed to a tunneler assembly including an elongate lance, each end of the lance configured to pierce tissue, and a handle configured to receive one end of the lance, the handle including a lance coupling for securing the end of the lance therein. The ends of the lance may include a needle or point for piercing tissue. In various aspects, the lance coupling is a quick connector. The lance coupling may include a collet adaptor. The lance coupling may include an actuator and locking device. The locking device may comprise a spring-loaded ring lock. The lock may be actuated by a switch or other element controlled by the user, or the lock may be engaged automatically by inserting the lance into the handle. The handle may include a gripping feature.

Various aspects of the invention are directed to an elongate lance having two ends, each end configured to pierce tissue, and an intermediate gripping feature.

Various aspects of the invention are directed to an adaptor for a tunneling system, the adaptor configured to connect a tissue piercing end of an elongate lance to a cable or a catheter. The adaptor may include a passageway sized and dimensioned to fit over the piercing end of the lance. The adaptor may be substantially tubular. One end of the adaptor may be sized and dimensioned to correspond to the piercing end. One end of the adaptor may be configured to radially expand and compress to secure to the piercing end. The adaptor may include engagement members configured to grasp the piercing end and form a secure connection thereto. The adaptor may include one or more through holes in a connecting portion of the adaptor. One end of the adaptor may include a connector for connecting the adaptor to a cable, catheter, or the like. The connector may be a screw thread.

In aspects of the invention, a surgical tunneler assembly comprises a lance including a first segment, a second end segment, and a connector on each one of the first end segment and the second end segment, further comprises a cable adapter including a lance connection portion and a cable connection portion, the lance connection portion configured to engage and disengage the connectors, the cable connection portion configured to engage and disengage an electrical cable, and further comprises a handle configured to engage and disengage the lance.

In other assembly aspects in combination with any one of the above assembly aspects, the lance connection portion includes a flexible device configured to deform and to engage and disengage the connectors.

In other assembly aspects in combination with any one of the above assembly aspects, either the lance connection portion the flexible device includes a lance passageway configured to radially expand to allow disengagement of the cable adapter from the connectors and to radially contract to allow engagement of the cable adapter to the connectors.

In other assembly aspects in combination with any one of the above assembly aspects, each of the connectors includes a narrow segment and a wide segment, and the lance passageway includes a constricted segment or an enlarged segment configured to engage the narrow segment or the wide segment respectively.

In other assembly aspects in combination with any one of the above assembly aspects, either the lance connection portion or the flexible device includes a plurality of engagement members configured to flex apart from each other and toward each other.

In other assembly aspects in combination with any one of the above assembly aspects, the cable adapter includes a ring configured to clamp around either one of the lance connection portion, the flexible device, the lance passageway, or the engagement members.

In other assembly aspects in combination with any one of the above assembly aspects, the ring includes an internal wall and a protrusion on or a depression into the internal wall configured to engage a depression into or protrusion on an outer surface of either one of the lance connection portion, the flexible device, the lance passageway, or the engagement members.

In other assembly aspects in combination with any one of the above assembly aspects, the cable connection portion includes a protrusion or a depression configured to engage the electrical cable.

In other assembly aspects in combination with any one of the above assembly aspects, the protrusion or the depression of the cable connection portion forms a helical thread.

In other assembly aspects in combination with any one of the above assembly aspects, the helical thread is disposed within the cable connection portion.

In other assembly aspects in combination with any one of the above assembly aspects, the cable connection portion includes a resilient device configured to form a liquid tight seal on the electrical cable when the cable connection portion is engaged to the electrical cable.

In other assembly aspects in combination with any one of the above assembly aspects, the resilient device is disposed within the cable connection portion.

In other assembly aspects in combination with any one of the above assembly aspects, the resilient device includes any one or a combination of an o-ring seal and a flat seal.

In other assembly aspects in combination with any one of the above assembly aspects, the handle is configured to engage and disengage the connectors.

In other assembly aspects in combination with any one of the above assembly aspects, the handle includes a tube having a passageway configured to receive the connectors, an actuator configured to move relative to the tube with application of an external force on the actuator, a lock member trapped within the tube, wherein the lock member is pushed into the passageway when the actuator is moved to a first position relative to the tube, and the lock member is capable of moving away from the passageway when the actuator is moved to a second position relative to the tube.

In other assembly aspects in combination with any one of the above assembly aspects, each of the connectors includes a depression configured to receive the lock member.

In aspects of the invention, a surgical implantation kit comprises an electrical device, an electrical cable including a first end connected to or configured for connection to the electrical device, and the surgical tunneler assembly of any one of the preceding assembly aspects.

In other kit aspects in combination with any one of the above kit aspects, the electrical device is a ventricular assist device or a controller for a ventricular assist device.

In other kit aspects in combination with any one of the above kit aspects, the kit further comprises a second electrical device connected to or configured for connection to a second end of the electrical cable.

In other kit aspects in combination with any one of the above kit aspects, the second electrical device is either a controller when the first electrical device is a ventricular assist device or a ventricular assist device when the first electrical device is a controller.

Various aspects of the invention are directed to a method of assembling an adaptor to a lance to form a tunneler assembly as described above. Various aspects of the invention are directed to a method of using a tunneler assembly, handle, lance, and/or adaptor as described above. The method can include attaching the handle to the lance; manipulating the handle to form a passageway through tissue in a patient requiring treatment; removing the handle from an end of the lance; attaching an adaptor over the end, the adaptor configured to carry a cable; securing a cable to the adaptor before or after the attaching; and pulling the lance carrying the cable through at least part of the passageway. In various embodiments, the manipulating includes pushing the lance through the tissue in one direction and the pulling includes pulling the lance in substantially the reverse direction.

The features and advantages of the invention will be more readily understood from the following detailed description which should be read in conjunction with the accompanying drawings.

DETAILED DESCRIPTION OF EXEMPLARY EMBODIMENTS

Figure 1:
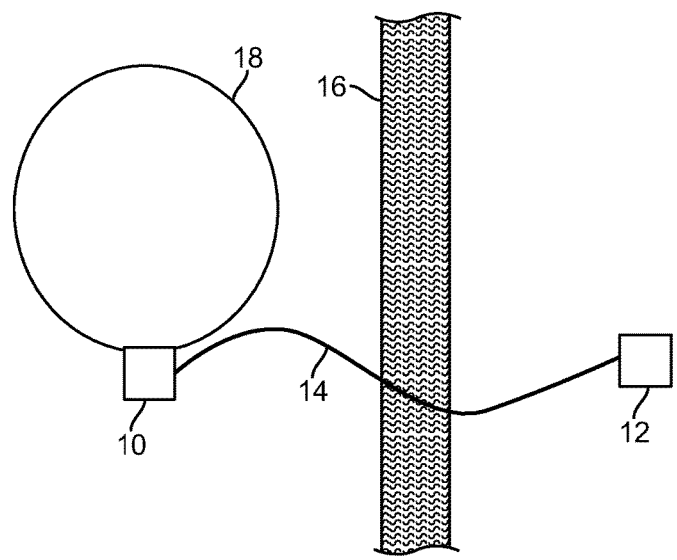
FIG. 1 is a block diagram showing exemplary electrical devices connected to each other by an electrical cable passing through the skin.

Referring now in more detail to the exemplary drawings for purposes of illustrating embodiments of the invention, wherein like reference numerals designate corresponding or like elements among the several views, there is shown in FIG. 1 internal electrical device 10 implanted within a human or animal body, and external electrical device 12 disposed outside the body. Internal electrical device 10 and external electrical device 12 are connected to each other by electrical cable 14 which passes through skin 16. Electrical cable 14 transmits electrical power and control signals from external electrical device 12 to internal electrical device 10. Internal electrical device 10 is attached to anatomical organ 18.

In some embodiments, internal electrical device 10 is a ventricular assist device attached to heart 18, and external electrical device 12 is an electronic controller configured to supply power, control, and monitor the ventricular assist device. The ventricular assist device includes a blood pump and is configured for attachment to the left ventricle of the heart. Suitable examples of a ventricular assist device include without limitation the pump devices described in connection with reference numeral 15 in U.S. Pat. No. 7,798,952 and reference numeral 1 in U.S. Pat. No. 7,850,594, both of which patents are incorporated herein for all purposes by reference. Other examples of ventricular assist devices include, but are not limited to, the devices described in U.S. Publication No. 2012/0046514 and U.S. Pat. No. 5,588,812, the entire contents of which are incorporated herein for all purposes by reference. Suitable examples of a controller include without limitation the devices described in connection with reference numeral 17 in U.S. Pat. No. 6,991,595 and reference numeral 10 in U.S. Pat. No. 7,850,594, both of which patents are incorporated herein for all purposes by reference.

In alternative embodiments, internal electrical device 10 is a cardiac pacemaker attached to heart 18.

In alternative embodiments, internal electrical device 10 is a sensor disposed within the body, and external electrical device 12 is a device configured to store, measure, and/or analyze a parameter detected by the sensor.

Suitable examples of electrical cable 14 include without limitation the percutaneous cable described in connection with reference numeral 14 in U.S. Publication No. 2012/0046515, which is incorporated herein for all purposes by reference.

Figure 2:
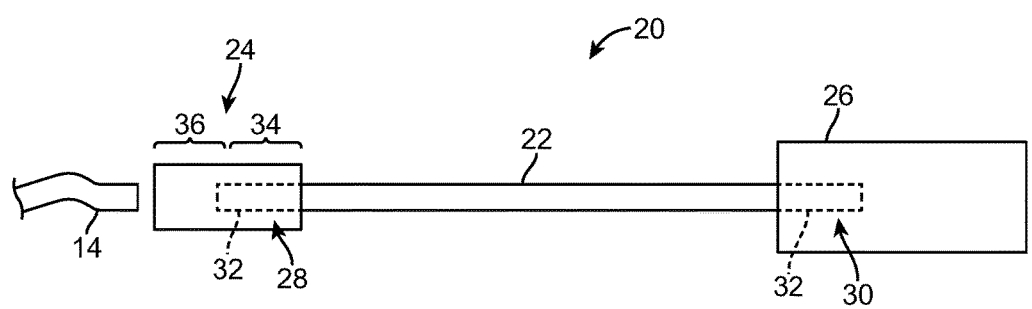
FIG. 2 is a block diagram showing an exemplary electrical cable and an exemplary tunneler assembly for passing the electrical cable through the skin.

Turning now to FIG. 2, a tunneler assembly in accordance with various aspects of the invention is shown. Aspects of the tunneler assembly may be similar to those described in U.S. Publication Nos. 2012/0083794 and 2012/0059321 and International Publication Nos. WO2003/008020 and WO2006/050191, the entire contents of which are incorporated herein for all purposes by reference.

In some embodiments, an implantation kit includes any one or both of electrical devices 10, 12, electrical cable 14, and tunneler assembly 20 as shown in FIG. 2.

In FIG. 2, tunneler assembly 20 includes lance 22, cable adapter 24, and handle 26. Cable adapter 24 and handle 26 are configured to engage on to and disengage from lance 22. Cable adapter 24 and handle 26 are capable of exchanging places with each other on lance 22.

Aspects of cable adaptor 24 may be similar to those described in U.S. Publication Nos. 2006/0030871 and 2005/0288762, the entire contents of which are incorporated herein for all purposes by reference.

In some embodiments, lance 22 is a rod of aluminum or stainless steel. Lance 22 can be made any metal, synthetic plastic, composite, or other material known in the art as being suitable for use in surgical instruments. Lance 22 can be about 16 inches in length, 24 inches in length, or another length depending on the patient, the region of the body on which the tunneling procedure is to be performed and/or the method of tunneling to be performed.

Figure 3:
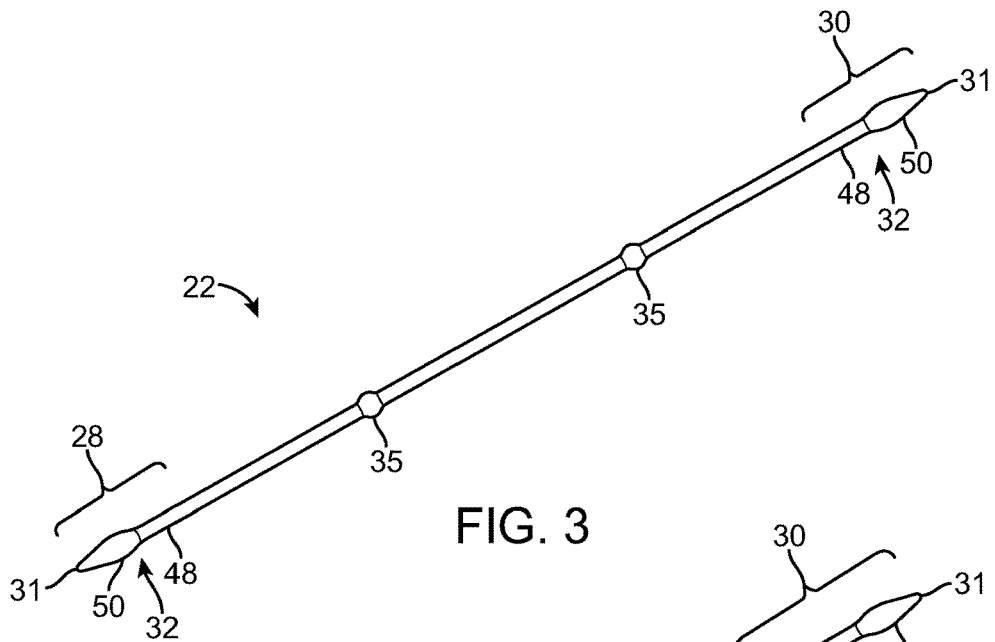
FIGS. 3 to 5 are perspective views of exemplary lances forming a part of a tunneler assembly.
Figure 4:
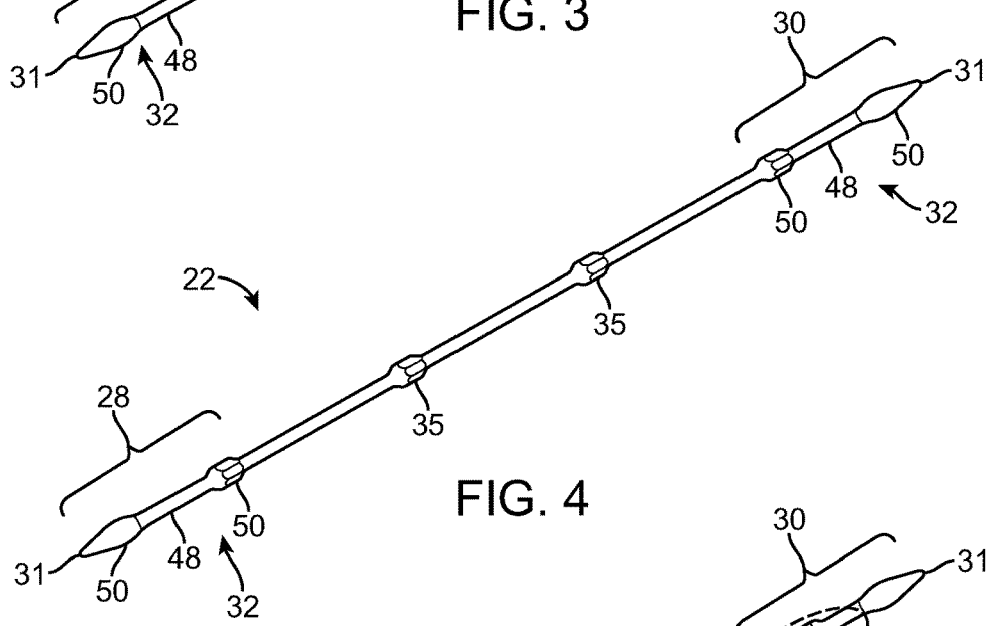
Figure 5:
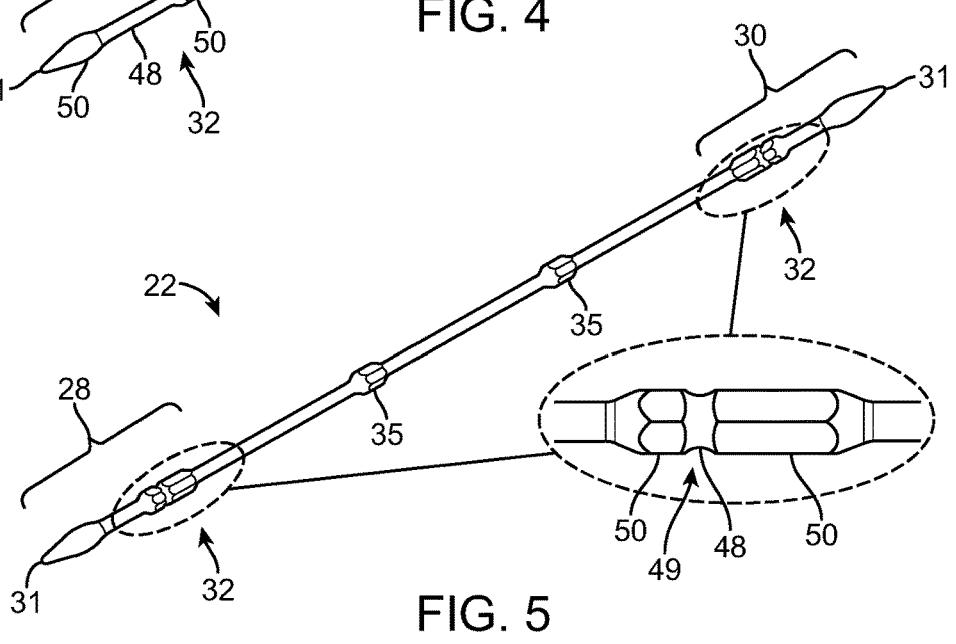

In some embodiments, lance 22 is as shown in any one of FIGS. 3 to 5. Lance 22 includes first end segment 28, second end segment 30, connector 32 on each one of first end segment 28 and second end segment 30, tapered tip 31 at the free end of each one of first end segment 28 and second end segment 30, and intermediate gripping features 35 spaced apart from each other along the axial length of lance 22. Tapered tip 31 facilitates passage of lance 22 through body tissue. The exemplary lance includes a pointed tip on each end to allow for bi-direction pushing through soft tissue. As will be described in further detail below, the lance and handle combination allow a clinician to comfortably and accurately create a path through soft tissue with fewer restrictions in terms of surgical technique compared to existing tunneler designs. For example, in the case of an open surgical procedure the tunneler system can be used to create a path from the inside out or from the outside in.

Connector 32 is configured to allow lance 22 to be selectively engaged onto and disengaged from cable adapter 24 and handle 26. Cable adapter 24 can be disconnected from first end segment 28 of lance 22 and connected to second end segment 30. Handle 26 can be disconnected from second end segment 30 of lance 22 and connected to first end segment 28. Lance 22 can be rigid, semi-rigid, or resiliently flexible. In some embodiments, lance 22 is malleable to allow plastic deformation of lance 22.

In alternative embodiments, lance 22 is identical or similar in shape to the malleable member described in connection with reference numeral 102 in U.S. Pat. No. 8,088,138, which is incorporated herein for all purposes by reference.

Referring again to FIG. 2, cable adapter 24 includes lance connection portion 34 and cable connection portion 36. Lance connection portion 34 is configured to engage and disengage connectors 32 on lance 22. Cable connection portion 36 is configured to engage and disengage electrical cable 14. When lance connection portion 34 is engaged on lance 22, cable adapter 24 is capable of rotating freely about its central axis 46 to prevent cable 14 from developing twists or kinks during performance of a tunneling method.

Figure 6A:
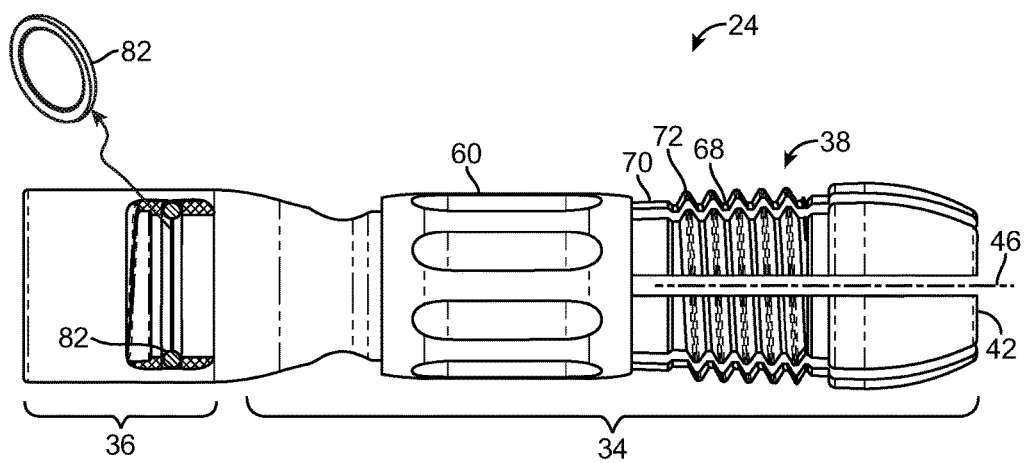
FIGS. 6A to 6C are plan, perspective, and cross-section views of an exemplary cable adapter forming a part of a tunneler assembly.
Figure 6B:
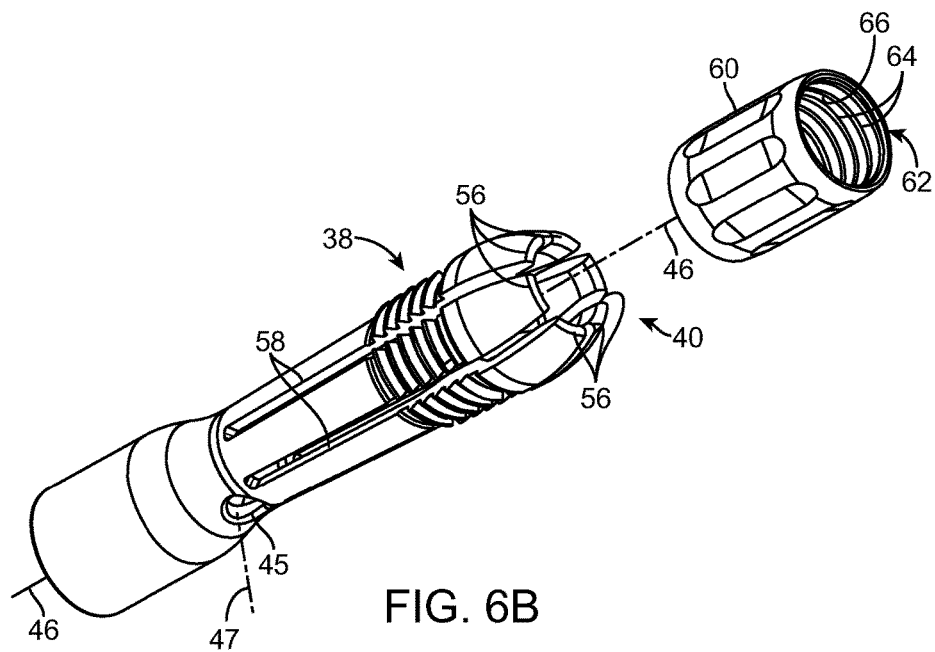
Figure 6C:
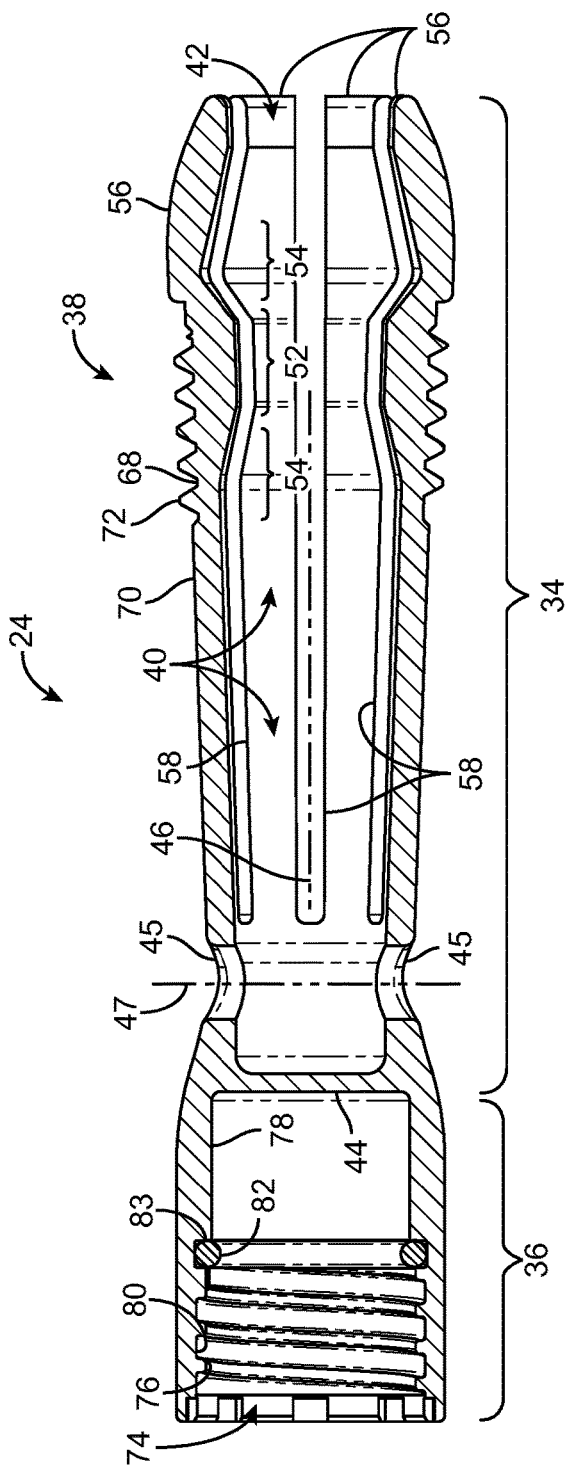

In some embodiments, cable adapter 24 is as shown in FIGS. 6A to 6C. Lance connection portion 34 includes flexible device 38 configured to elastically deform and to engage and disengage connectors 32 of lance 22. Flexible device 38 defines lance passageway 40 extending into cable adapter 24. Passageway 40 includes opening 42 and septum wall 44 (FIG. 6C) located opposite and coaxially aligned with opening 42 along central axis 46 of cable adapter 24. Passageway 40 is configured to radially expand to allow cable adapter 24 to disengage from connectors 32 of lance 22 and to radially contract to allow cable adapter 24 to engage connectors 32. A pair of through holes 45 is formed through lance connection portion 34. Through holes 45 can be used to tie cable adapter 24 to cable 14 when packaged in a sealed tray so that when the tray is opened in preparation for an implantation procedure, the cable adapter 24 does not inadvertently fall on the floor. Through holes 45 are aligned along transverse axis 47 perpendicular to central axis 46.

Referring again to FIGS. 3 to 5, each of connectors 32 of lance 22 includes narrow segment 48 and wide segment 50 that are immediately adjacent to each other. There may be multiple narrow segments 48 and multiple wide segments 50. Narrow segment forms recess 49 located adjacent wide segment 50 or between pairs of wide segments 50.

As shown in FIG. 6C, lance passageway 40 includes constricted segment 52 and enlarged segments 54 surrounding constricted segment 52. The diameter of lance passageway 40 is smaller at constricted segment 52 than at enlarged segments 54. Constricted segment 52 is configured to engage narrow segment 48 of lance 22. Enlarged segment is configured to receive and/or engage wide segment 50 of lance 22.

As shown in FIGS. 6A to 6C, flexible device 38 of cable adapter 24 includes a plurality of engagement members 56 configured to flex apart from each other and toward each other. Engagement members 56 are arranged circumferentially around passageway 40. Each engagement member 56 is spaced apart by axial slot 58 from adjacent engagement members 56. Slots 58 provide spaces which allow engagement members 56 to collapse toward each other, which causes constriction of passageway 40 and causes constricted segment 52 and enlarged segments 54 of passageway 40 to engage narrow segment 48 and wide segment 50 of lance 22.

As shown in FIGS. 6A and 6B, cable adapter 24 includes ring 60. Ring 60 is omitted from FIG. 6C. Ring 60 is configured to clamp around engagement members 56. Ring 60 includes internal wall 62, protrusion 64 on internal wall 62, and grooves or depression 66 into internal wall 62. Protrusion 64 is integrally formed on internal wall 62 and is configured to engage depression 68 formed into outer surface 70 of each engagement member 56. Depression 66 of ring 60 is configured to receive and engage protrusion 72 integrally formed on outer surface 70 of each engagement member 56. Protrusion 64 and depression 66 of ring 60 forms an internal helical thread on internal wall 62. Protrusion 72 and depression 68 on engagement members 56 form an external helical thread interrupted by slots 58. The external helical thread on engagement members 56 mates with the internal helical thread on ring 60.

As shown in FIG. 6C, cable connection portion 36 of cable adapter 24 includes blind hole 74 configured to receive an end segment of electrical cable 14. Protrusion 76 is integrally formed on internal wall 78 of blind hole 74. A groove or depression 80 is formed into internal wall 78. Internal wall 78 is annular, and protrusion 76 and depression 80 form a helical thread within blind hole 74.

As shown in FIGS. 6A and 6C, cable connection portion 36 includes a resilient device in the form of o-ring seal 82 made of synthetic rubber, silicone, or other resilient material. In FIG. 6, a cutaway window is presented for illustration purposes to show o-ring seal 82. The cutaway window does not actually exist on cable connection portion 36. O-ring seal 82 is retained within annular groove 83 formed into internal wall 78. O-ring seal 82 forms a liquid tight seal on electrical cable 14 when cable connection portion 36 is engaged to electrical cable 14.

Figure 7:
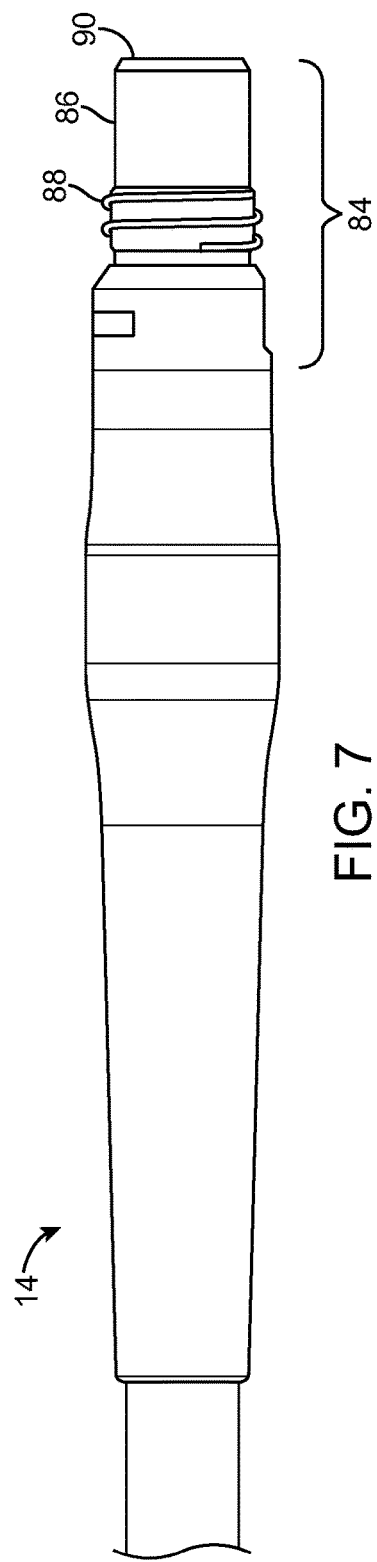
FIG. 7 is a plan view showing an end segment of an exemplary electrical cable.

In some embodiments, electrical cable 14 is as shown in FIG. 7. End segment 84 of electrical cable 14 includes cylindrical wall 86 and external helical thread 88. O-ring seal 82 of cable adapter 24 encircles and presses against cylindrical wall 86. O-ring seal 82 is compressed between cylindrical wall 86 of electrical cable 14 and internal wall 78 of cable adapter 24.

In an exemplary adapter-to-cable connecting method, end segment 84 of electrical cable 14 is pushed into blind hole 74 of cable adapter 24 until external helical thread 88 of electrical cable 14 abuts the internal thread formed by protrusion 76 and depression 80 within blind hole 74. Next, cable adapter 24 is twisted about its central axis 46. Twisting can be accomplished by manually by grasping the body of cable adapter 24 and then rotating cable adapter 24 about central axis 46 so that the external and internal threads helically engage each other and force end segment 84 of electrical cable 14 further into blind hole 74. As end segment 84 moves further into blind hole 74, o-ring seal 82 encircles and presses against cylindrical wall 86 of end segment 84. When end opening 90 is axially disposed between o-ring seal 82 and septum wall 44, electrical contacts housed within end segment 84 and which are accessible through end opening 90 are protected from any liquid which may be present outside cable adapter 24 during a surgical procedure.

Next, in an exemplary adapter-to-lance connecting method, any one of first end segment 28 and second end segment 30 of lance 22 is inserted into passageway 40 in lance connection portion 34 of cable adapter 24 while ring 60 is at a retracted position shown in FIG. 6A. As lance 22 is inserted into passageway 40, engagement members 56 flex radially outward as constricted segment 52 of passageway 40 passes over wide segment 50 of connector 32 on lance 22, and then move radially inward as constricted segment 52 becomes seated around narrow segment 48 of lance 22. While constricted segment 52 is seated around narrow segment 48, ring 60 is pushed by the user into contact with the external thread formed by depression 68 and protrusion 72 on outer surface 70 of engagement members 56. Upon contact, ring 60 is rotated about central axis 46 which brings ring 60 to an extended position over constricted portion 52. Ring 60 now prevents engagement members 56 from flexing radially outward, which keeps the inserted connector 32 of lance 22 locked within lance connection portion 34 of cable adapter 24.

In the exemplary embodiment, no tools are necessary to attach cable adapter 24 to electrical cable 14 and to lance 22. One of skill will appreciate from the description herein, however, that the adaptor can be modified for use with standard or customized tools. One will also appreciate that the adaptor can be modified to carry other components such as catheters and data cables.

Figure 8A:
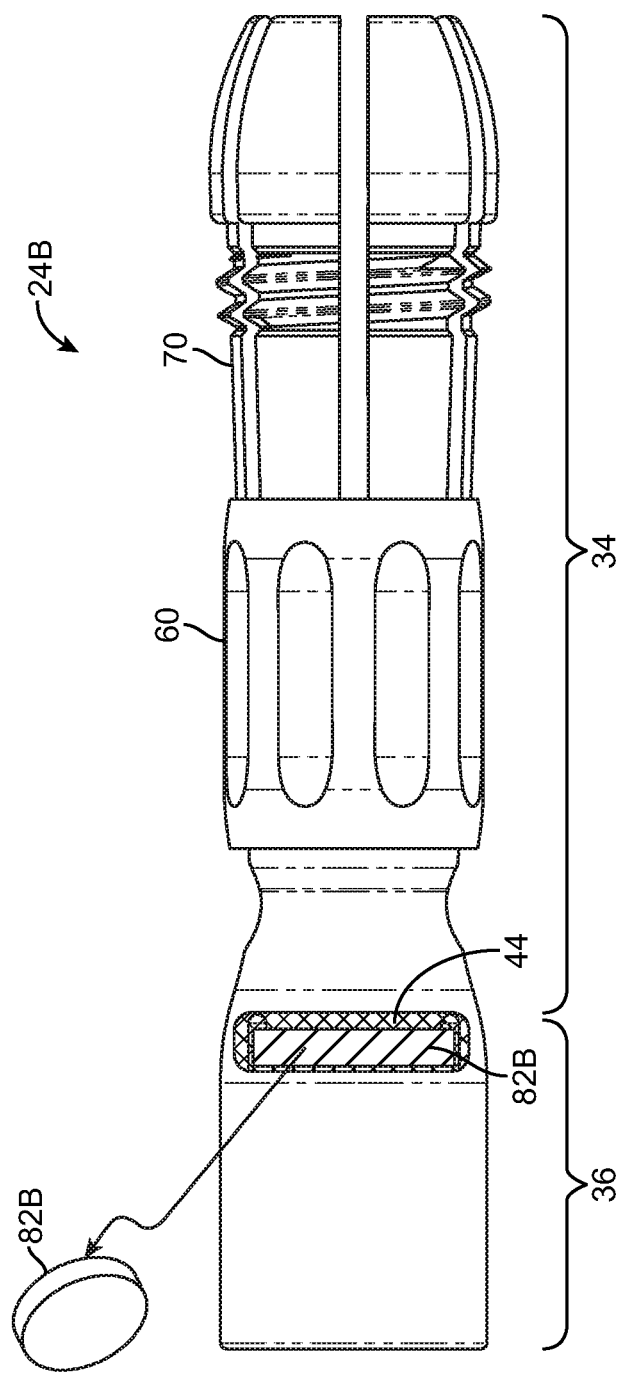
FIG. 8A is a plan view of an exemplary cable adapter forming a part of a tunneler assembly.
Figure 8B:
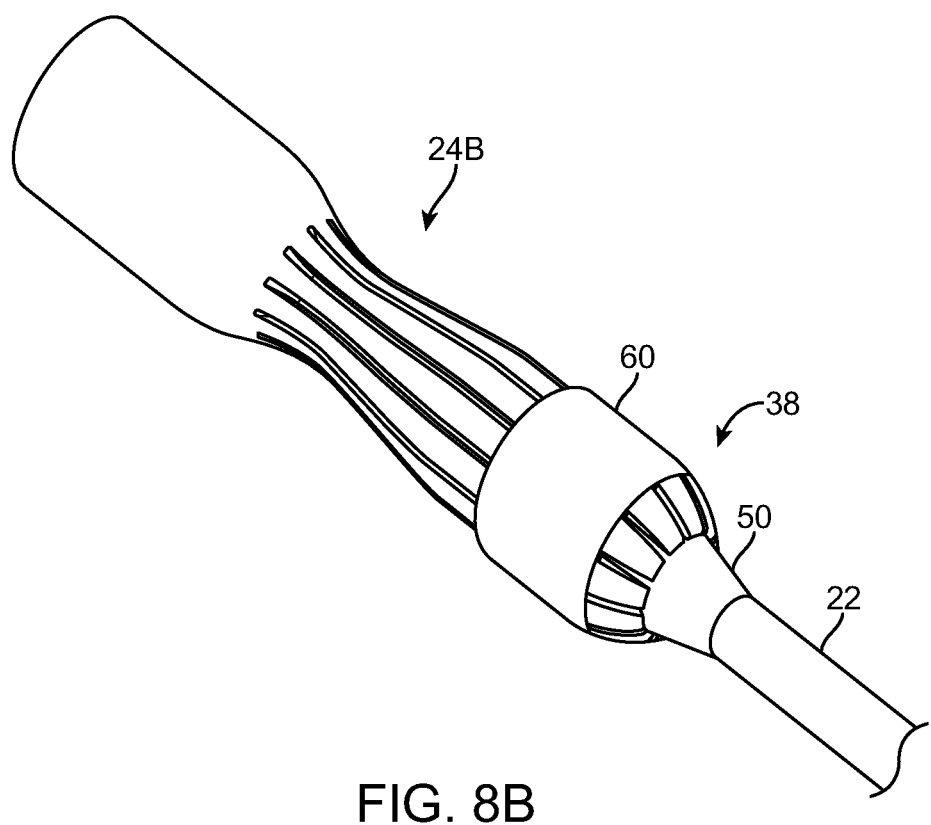
FIG. 8B is a perspective view of the cable adaptor connected to a lance, illustrating the adaptor in a locked position.

In alternative embodiments, cable adapter 24B is as shown in FIGS. 8A-8B. Lance connection portion 34 is identical to that of FIGS. 6A to 6C, except a lesser number of turns of the external thread on outer surface 70 are present in FIGS. 8A-8B. Cable connection portion 36 is identical to that of FIGS. 6A to 6C, except the resilient device for sealing against electrical cable 14 is in the form of flat seal 82B made of synthetic rubber, silicone, or other resilient material. Flat seal 82B is disposed against septum wall 44 as shown through the cutaway window. The cutaway window does not actually exist on cable connection portion 36 and is presented for illustration purposes to show the location of flat seal 82B.

Cable adapter 24B is functionally identical to cable adapter 24 of FIGS. 6A to 6C, except sealing is achieved differently. In an exemplary adapter-to-cable connecting method, as end segment 84 of electrical cable 14 moves further into blind hole 74 with twisting of cable adapter 24, forward edge of end opening 90 of electrical cable 14 presses against flat seal 82B. When forward edge of end opening 90 is pressed against flat seal 82B, electrical contacts housed within end segment 84 and which are accessible through end opening 90 are protected from any liquid which may be present outside cable adapter 24 during a surgical procedure.

FIG. 8B shows cable adapter 24B of FIG. 8A after ring 60 is moved into the lock position. Pull action by the user places ring 60 in tension. Push action by the user maintains the lock position of ring 60 via tissue friction.

Referring to FIG. 8B, in some embodiments, a protrusion and/or depression forms a snap feature on the outer surface of flexible device 38 of cable adapter 24B, and the internal wall of ring 60 has a corresponding snap feature configured to mate with and/or engage the snap feature on flexible device 38. The user advances ring 60 linearly toward and over the snap feature on flexible device 38 so that ring 60 is locked in position over flexible device 38 and prevents lance 22 from pulling out of flexible device 38. The snap features on flexible device 38 and ring 60 can be configured so that ring 60 need not be twisted relative to flexible device 38 in order to lock ring 60 over flexible device 38.

In alternative embodiments, the resilient device for sealing against electrical cable 14 includes o-ring seal 82 as described in connection with FIGS. 6A to 6C and flat seal 82B as described in connection with FIG. 8A.

Figure 9A:
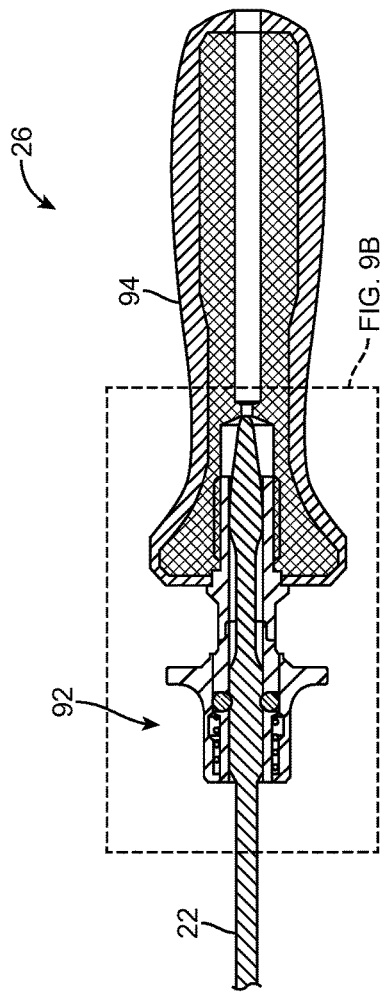
FIGS. 9A and 9B are cross-section and detailed cross-section views showing an exemplary end segment of a lance locked within an exemplary connection device of a handle.
Figure 9B:
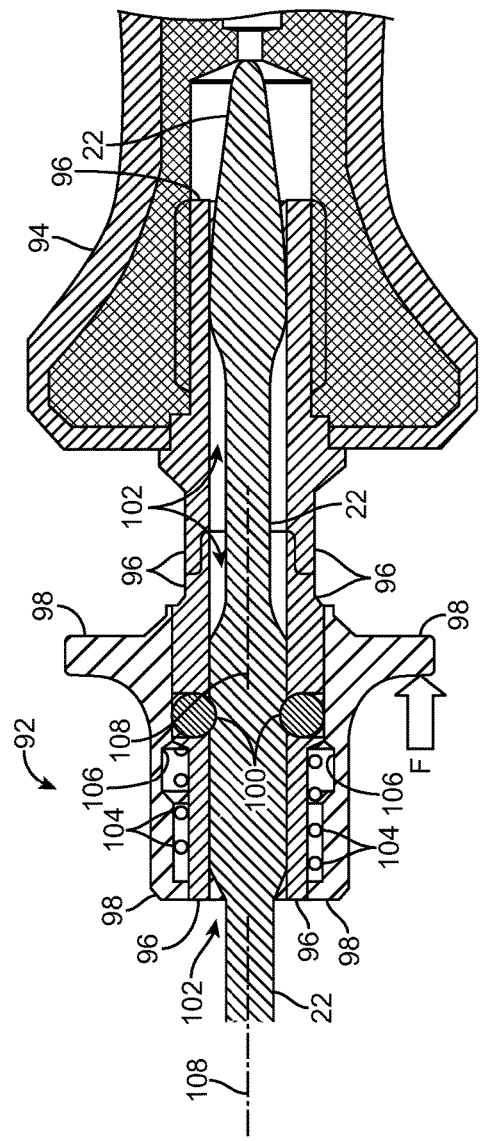

In some embodiments, handle 26 is as shown in FIGS. 9A and 9B. Handle 26 includes lance coupling device 92 and grip 94. Lance coupling device 92 includes tube 96, actuator 98, and lock member 100. Tube 96 is fixedly mounted into grip 94. Tube 96 has passageway 102 configured to receive any of the first end segment 28 and second end segment 30 of lance 22. Actuator 98 is configured to move relative to tube 96 and grip 94 when external force F is axially applied on actuator 98.

Lock member 100 is trapped within tube 96. Lock member 100 can be a ring or a ball. Lock member 100 is pushed into the passageway when actuator 98 is moved to an extended or first position relative to tube 96, as shown in FIG. 9B. Coil spring 104 is trapped between tube 96 and actuator 98. Coil spring 104 is under compression and continuously urges actuator 98 to move to the first position.

Depression 106 is formed into actuator 98. When actuator 98 is in the first position, as shown in FIG. 9B, depression 106 is axially spaced apart from lock member 100, which prevents lock member from moving radially outward away from central axis 108 of passageway 102. When the user pulls actuator 98 toward grip 94 with application of force F, coil spring 104 is compressed further and actuator 98 is moved to a retracted or second position relative to tube 96. When actuator 98 is in the second position, depression 106 is aligned with and disposed over lock member 100, which allows lock member 100 to move radially outward and away from central axis 108.

In alternative embodiments, handle 26 is identical or similar in configuration to the handle described in connection with reference numeral 112 in U.S. Pat. No. 8,088,138, which is incorporated herein for all purposes by reference.

Figure 10:
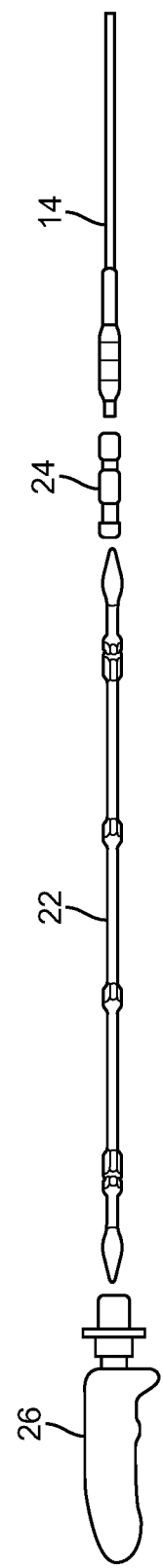
FIG. 10 is an assembly view of an exemplary tunneler assembly in accordance with aspects of the invention, illustrating a lance, a handle, and a cable adaptor carrying a percutaneous cable.

FIG. 10 shows an exemplary tunneler assembly having quick connect handle 26, tunneler 22 with gripping features (such as shown in FIG. 5), and collet cable adaptor 24 (such as shown in FIGS. 6A and 8A) for carrying driveline 14 (such as a percutaneous cable).

In an exemplary lance attachment method, a user moves actuator 98 to its second position and holds it while lance 22 is pushed into passageway 102. As wide segment 50 of lance 22 passes across lock member 100, lock member 100 moves into depression 106 of actuator 98. When the tip of lance 22 abuts stop 108 within grip 94, narrow segment 48 of lance 22 is axially aligned with lock member 100. Upon contacting the tip of lance 22 with stop 108, the user releases actuator 98. Coil spring 104 causes actuator 98 to return to its first position (FIG. 9B), which moves depression 106 away from lock member 100. Lock member 100 is forced onto narrow segment 48 of lance 22. Because depression 106 is no longer aligned with lock member 100, lock member 100 cannot disengage narrow segment 48, which prevents wide segment 50 of lance 22 from pulling out of tube 96. To release lance 22 from tube 96, the user moves actuator 98 to its second position and holds it there while lance 22 is pulled out, during which time lock member 100 moves in a radially outward direction as wide segment 50 of lance 22 slides past lock member 100 and out of tube 96.

It will be appreciated that tunneler assembly 20 provides the user with the ability to selectively attach and remove handle 96 and cable adapter 24 to any end segment 28, 30 of lance 22. This allows for flexibility in surgical method.

Figure 11:
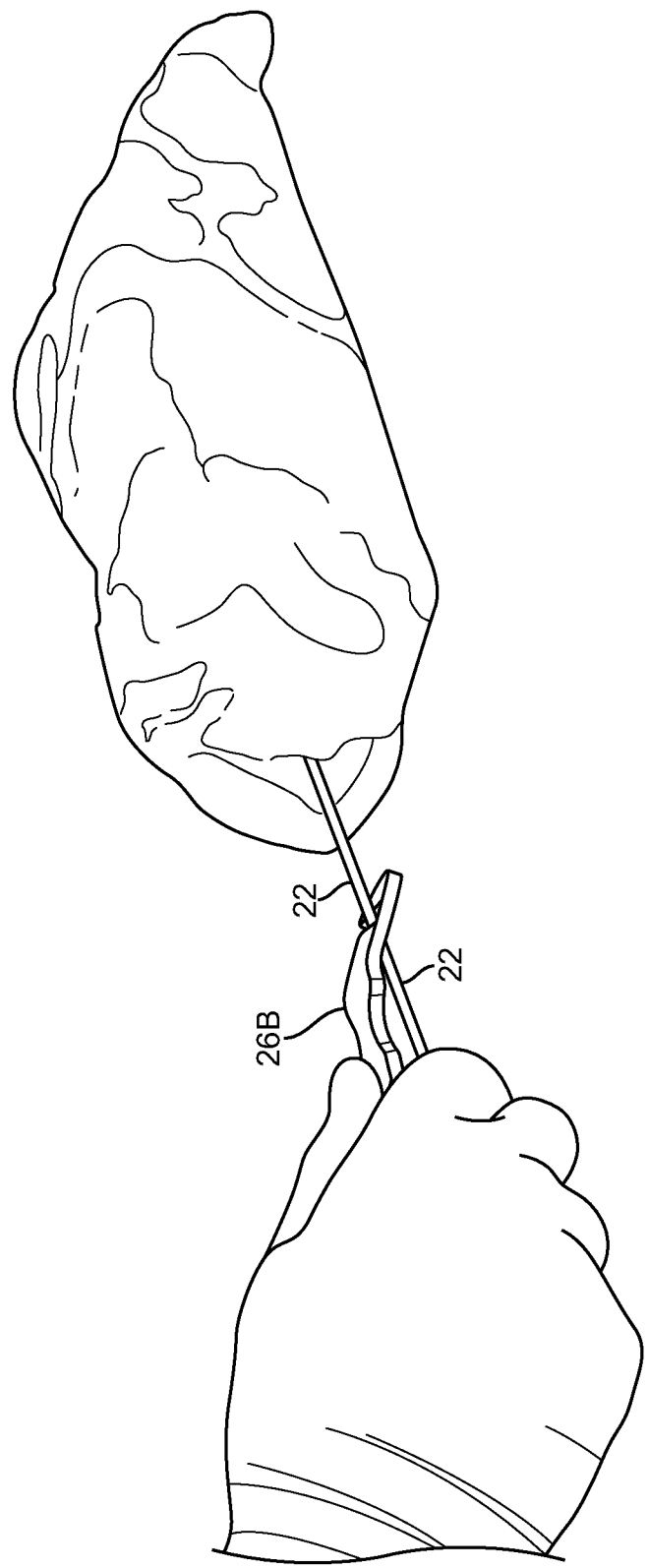
FIGS. 11-13 show an exemplary method of using the tunneler assembly of FIG. 10.
Figure 12:
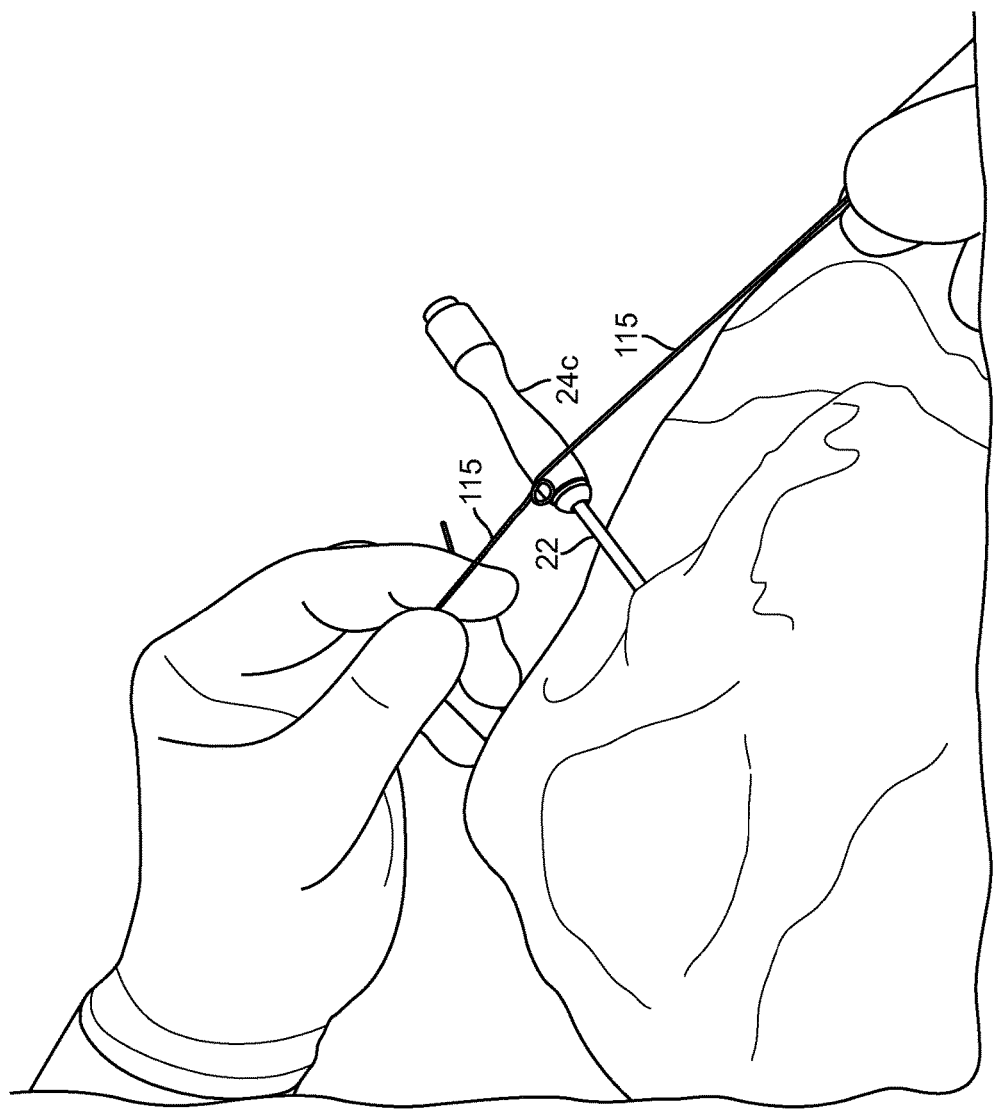
Figure 13:
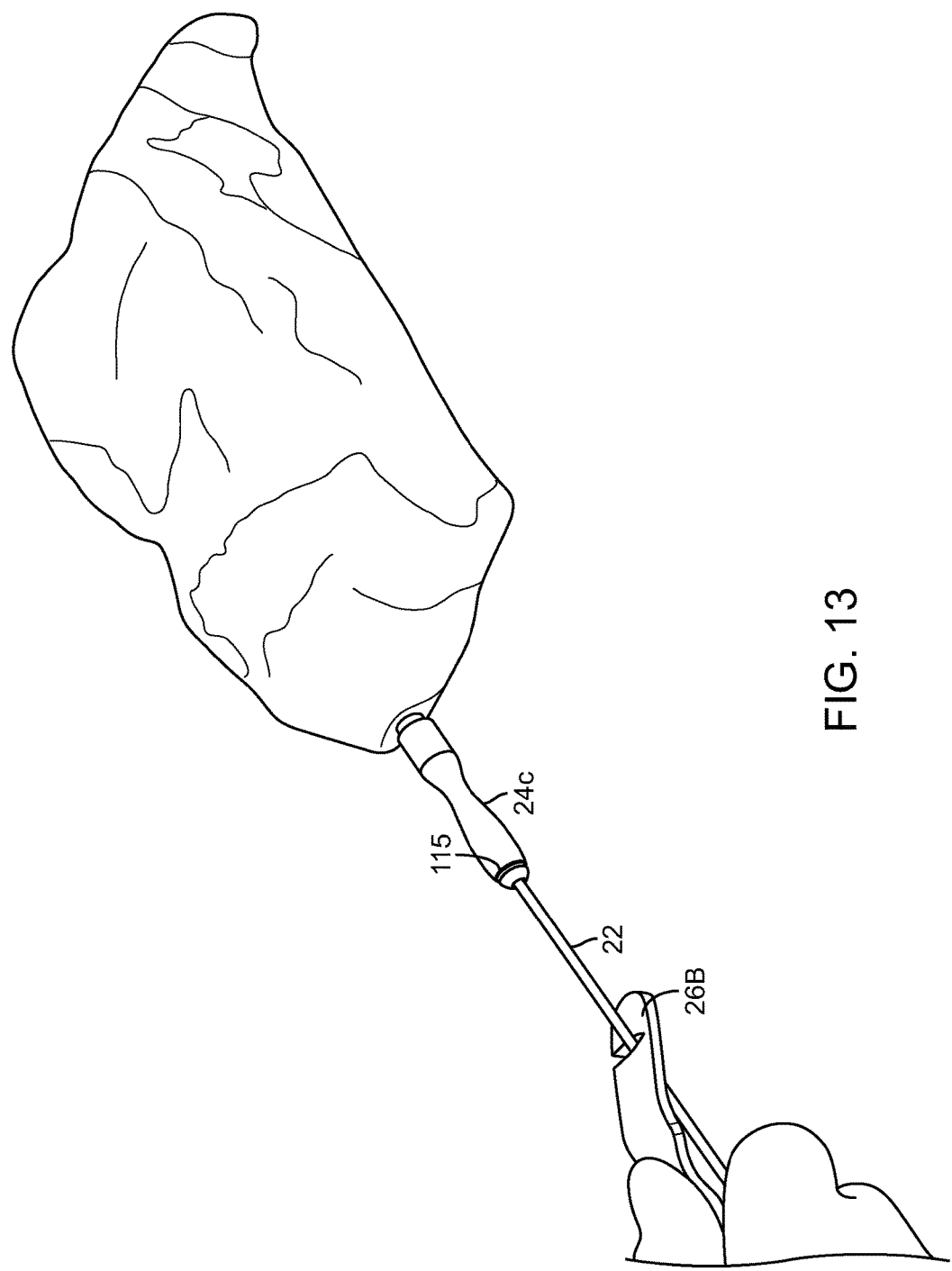

With reference to FIGS. 11 to 13, in an exemplary surgical tunneling method, end segment 84 of electrical cable 14 is pulled out from within the body of the patient using tunneler assembly 20, which may be accomplished as follows. Lance 22 is placed outside the body of the patient with handle 26 attached to one of the end segments 28, 30 of lance 22 according to the exemplary lance attachment method described above or other method. The opposite end segment of lance 22 is pushed through the skin and into the body of the patient. At any prior time during the surgical tunneling method, cable adapter 24 and electrical cable 14 are connected together according to the exemplary adapter-to-cable connecting method described above or other method. For example, the adapter-to-cable connecting method may include twisting cable adapter 24 relative to electrical cable 14 to attach and seal end segment 84 of electrical cable 14 within cable adapter 24. Thereafter, cable adapter 24 is connected to lance 22 according the exemplary adapter-to-lance connecting method described above or other method. For example, the adapter-to-lance connecting method may include twisting or sliding ring 60 relative to flexible device 38 in order to tighten ring 60 over flexible device 38. It will be appreciated that adapter-to-lance connecting method may be performed before or after the adapter-to-cable connecting method. Next, the user pulls electrical cable 14 from inside the patient's body, through the skin, and out of the patient's body by pulling handle 26 which remains attached to the same end segment of lance 22. Cable adapter 24 is released from lance 22 by unscrewing and loosening ring 60 from flexible device 38. Next, cable adapter 24 is twisted relative to electrical cable 14 to disconnect it from electrical cable 14.

In another exemplary surgical tunneling method, end segment 84 of electrical cable 14 is pulled into the body of the patient using tunneler assembly 20, which may be accomplished as follows. Lance 22 is placed outside the body of the patient with handle 26 attached to one of the end segments 28, 30 of lance 22 according the exemplary lance attachment method described above or other method. The opposite end segment of lance 22 is pushed through the skin and into the body of the patient. With electrical cable 14 located outside the patient's body, cable adapter 24 is connected to electrical cable 14 either before or after cable adapter 24 is connected to lance 24. Handle 26 is removed from lance 22 and is replaced by cable adapter 24 on the same end segment of lance 22. Handle 26 is attached to the opposite end segment of lance 22. The user then pulls electrical cable 14 from outside the patient's body, through the skin, and into the body by pulling handle 26. Cable adapter 24 is released from lance 22 by unscrewing and loosening ring 60 from flexible device 38. Next, cable adapter 24 is twisted relative to electrical cable 14 to disconnect it from electrical cable 14.

In yet another exemplary surgical tunneling method, end segment 84 of electrical cable 14 is pulled out from inside the body of the patient using tunneler assembly 20, which may be accomplished as follows. One of the end segments 28 of lance 22 is positioned inside the body of the patient with handle 26 attached to the opposite end segment 30 of lance 22 according the exemplary lance attachment method described above or other method. Tip 31 of end segment 28 is pushed from inside the body, through the skin, and to the exterior of the body. Handle 26 is removed from lance 22 and is replaced by cable adapter 24 on end segment 30 of lance 22. Cable adapter 24 is connected to electrical cable 14 either before or after cable adapter 24 is connected to lance 24. Handle 26 is attached to end segment 28 of lance 22 which was previously pushed through the skin and is now outside the patient's body. The user then pulls handle 26 away from the body which causes electrical cable 14 to be pulled from inside the patient's body, through the skin, and out of the body. Cable adapter 24 is released from lance 22 by unscrewing and loosening ring 60 from flexible device 38. Next, cable adapter 24 is twisted relative to electrical cable 14 to disconnect it from electrical cable 14.

One of skill in the art will appreciate from the description herein that the tunneler assembly may be modified to suit different procedures and other design needs.

Figure 14:
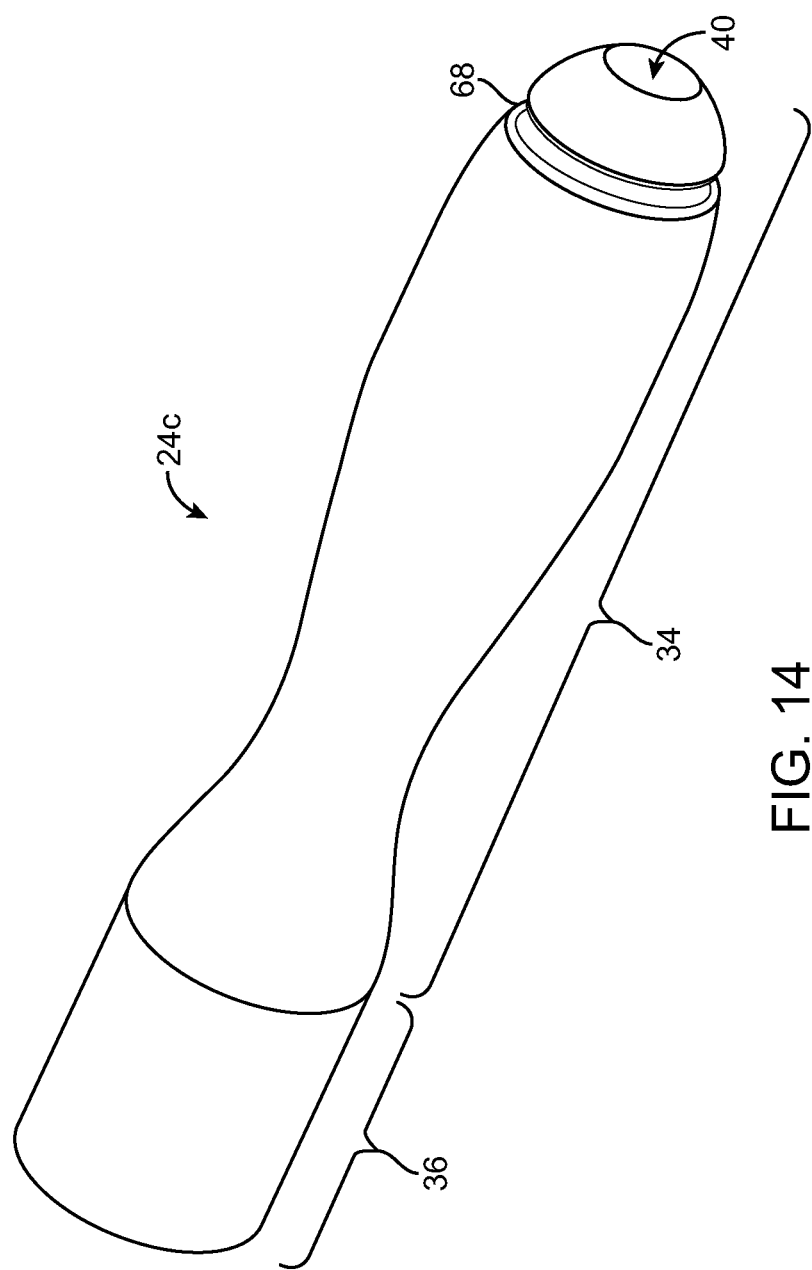
FIGS. 14-16 show a perspective view of a cable adapter, a perspective partial cross-sectional of the cable adapter, and a perspective view of a cable connection portion of the cable adaptor in accordance with aspects of the invention.
Figure 15:
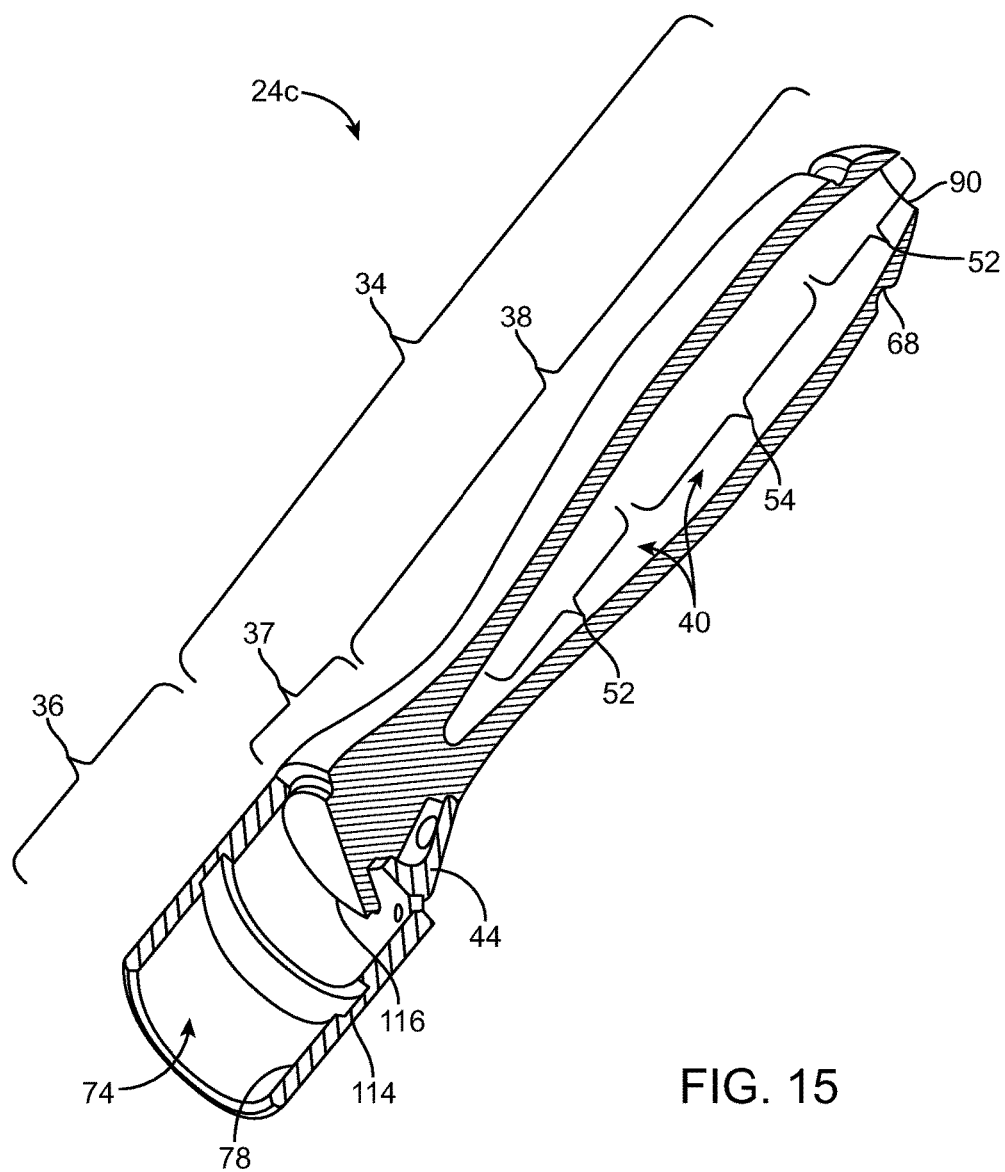
Figure 16:
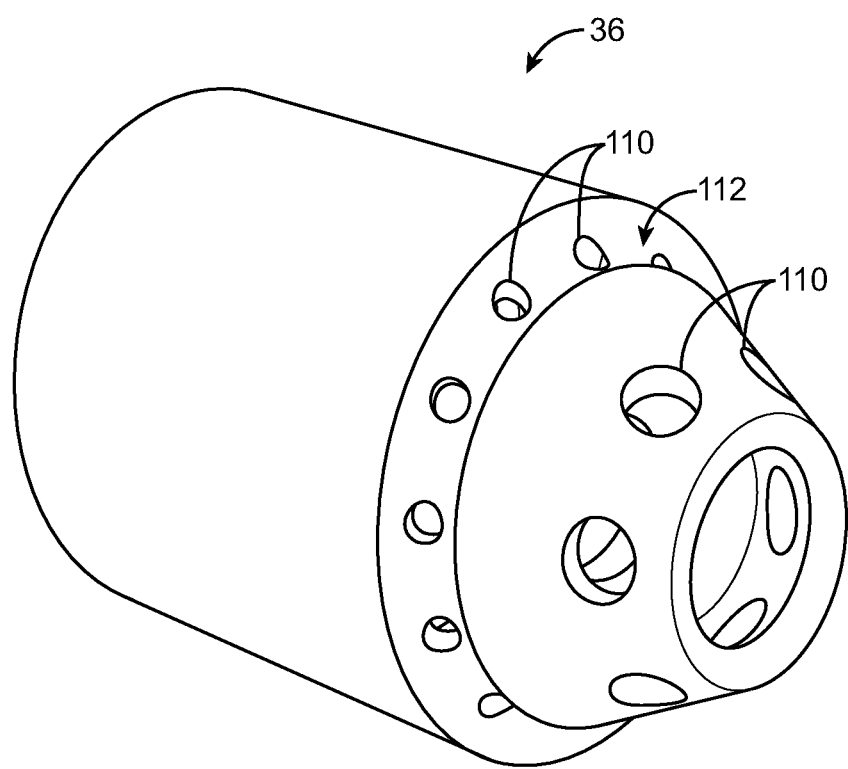

In some embodiments, the cable adapter is as shown in FIGS. 14-16. Cable adapter 24C includes cable connection portion 36 made of a substantially rigid material, such as aluminum, stainless steel, or other material. Cable adapter 24C includes lance connection portion 34 made of an elastomeric material that is flexible and capable elastic deformation. Connection portion 34 includes interface segment 37 and flexible device 38.

Interface segment 37 of lance connection portion 34 is fixedly attached to cable connection portion 36. For example, cable connection portion 36 can be inserted in a mold in the shape of lance connection portion 34 and molten material for the lance connection portion 34 can be introduced into the mold. The molten material flows through a hole formed through septum wall 44 and into through holes 110 and grooves 102 (FIG. 16) formed through lance connection portion 34. Upon solidification of the molten material, lance connection portion 34 is fully formed and permanently attached to cable connection portion 36.

Flexible device 38 includes lance passageway 40 that includes constricted segments 52 and enlarged segment 54. The diameter of passageway 40 is smaller in constricted segments 52 than in enlarged segment 54. The inner surface of constricted segment 52 and enlarged segments 54 combined has a shape that matches and mates with the shape of the outer surface of connector 32 of lance 22. Annular groove or depression 68 is formed in outer surface 70 of flexible device 38. Depression 68 is located around constricted segment 52 adjacent to end opening 90 of lance passageway 40.

In alternative embodiments, flexible device 38 includes a plurality of axially extending engagement members similar to engagement members 56 in FIG. 6B.

In alternative embodiments, flexible device 38 includes one or more axially extending slots similar to slots 58 in FIG. 6B.

Referring to FIG. 15, blind hole 74 extends into cable connection portion 36 and is configured to receive an end segment of cable 14. Annular groove or depression 114 is formed into inner surface 78 of cable connection portion 36. Depression 114 may be configured to engage and retain the end segment of cable 14 or may be configured to receive and retain an o-ring seal similar to o-ring seal 82 in FIG. 6C for providing a water-tight seal around the end segment of cable 14. End segment 116 of lance connection portion 34 extends through the hole in septum wall 44 and into blind hole 78. End segment 116 has a flat surface and may serve the same function as flat seal 82B in FIG. 8 for providing a water-tight seal on end opening 90 of cable 14.

In alternative embodiments, inner surface 78 of cable connection portion 36 includes an internal helical thread for engaging and retaining end segment 84 of cable 14.

In an exemplary adapter-to-lance connecting method, any one of first end segment 28 and second end segment 30 of lance 22 is inserted into passageway 40 in lance connection portion 34 of cable adapter 24C. As lance 22 is inserted into passageway 40, flexible device 38 expands radially outward as wide segment 50 of connector 32 of lance 22 passes through constricted segment 54 of passageway 40 adjacent to end opening 90, and then autonomously contracts as wide segment 50 of lance 22 is received within enlarged segment 54 of passageway 40. Next, a piece of string or lacing 115 (FIG. 12) is wrapped around and into depression 68, and then tightened and tied to prevent loosening. Lacing 115 prevents constricted segment 54 adjacent to end opening 90 from expanding, which keeps connector 32 of lance 22 locked within lance connection portion 34 of cable adapter 24C until the lacing is cut or untied.

Figure 17:
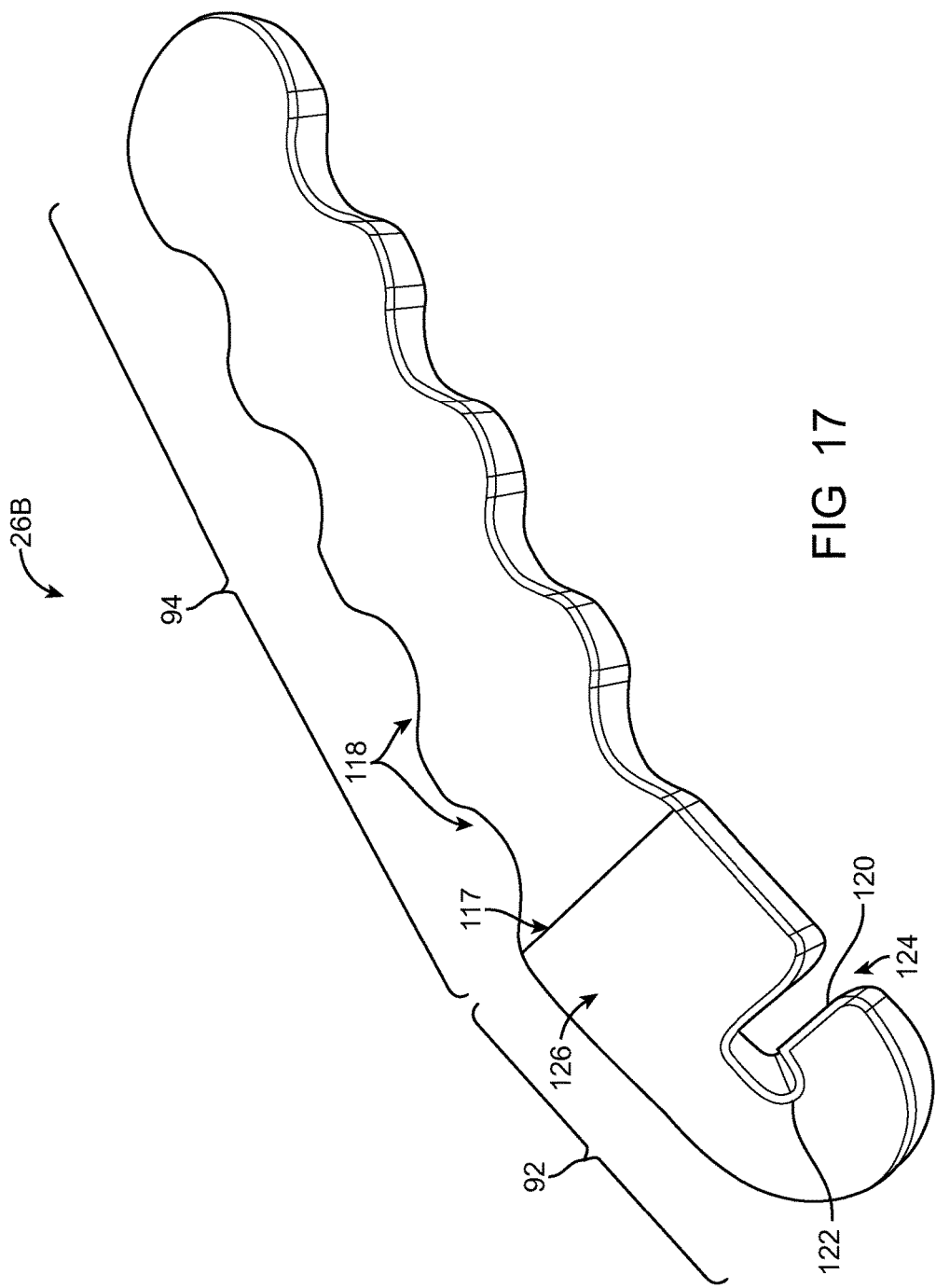
FIGS. 17-19 are perspective views showing a handle (FIG. 17) in accordance with aspects of the invention, the handle attached to the lance (FIG. 18), and the handle attached to the lance with cable adapter (FIG. 19).
Figure 18:
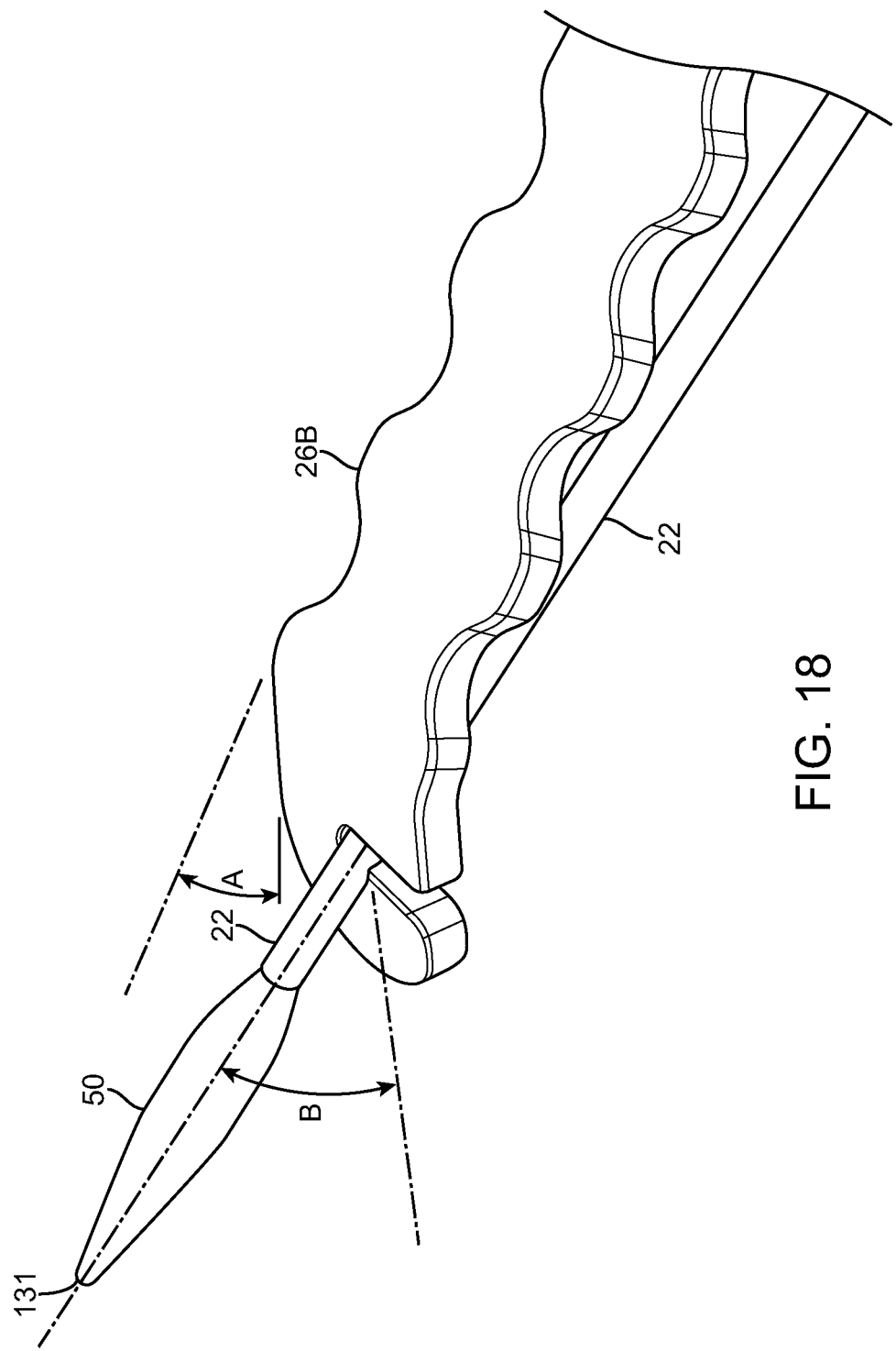
Figure 19:
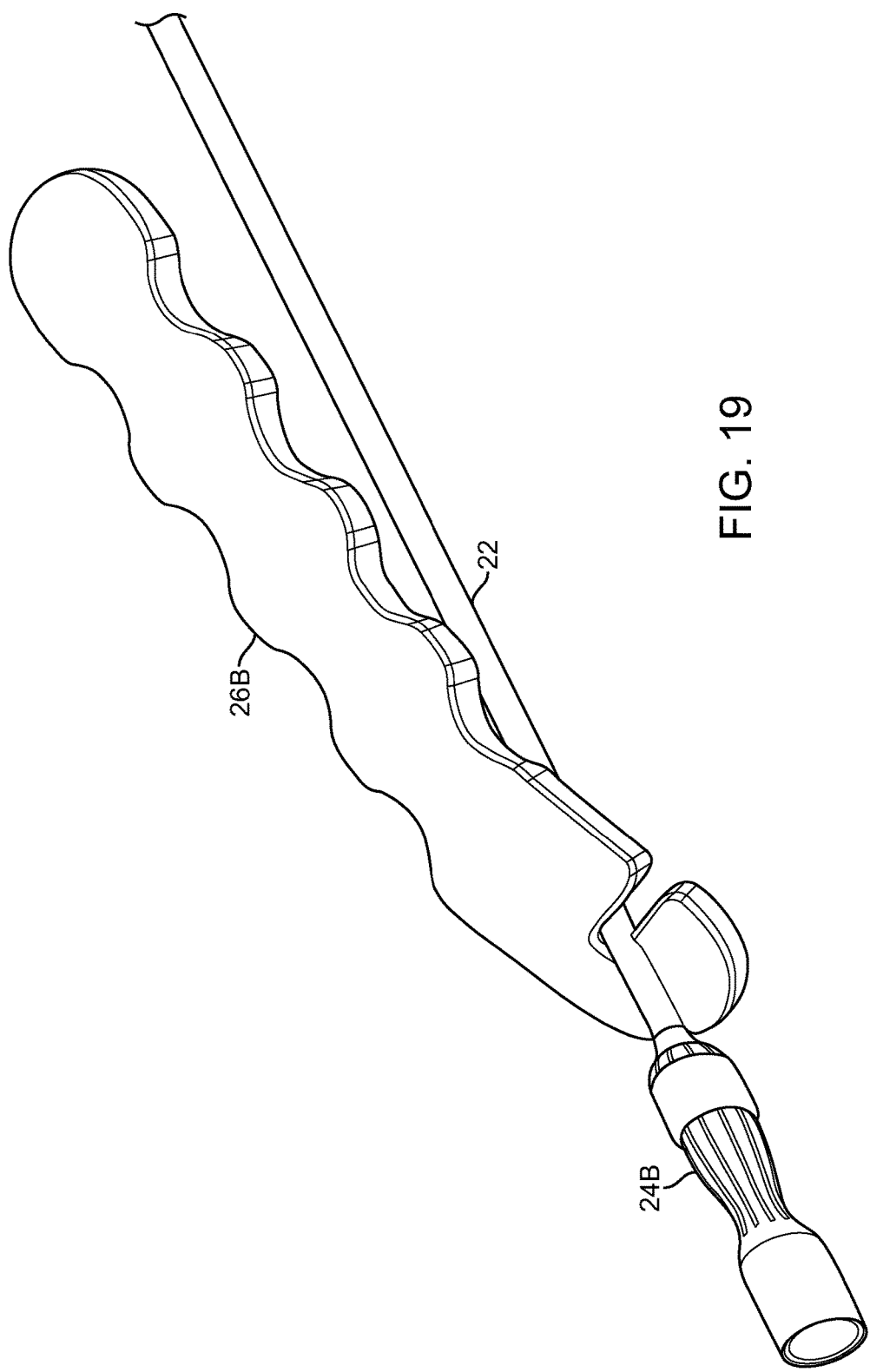

FIGS. 17-19 show handle 26B configured to engage onto and disengage from lance 22 at any number of locations along the axial length of lance 22. Handle 26B is in the shape of a flat bar and includes lance coupling device 92 and grip 94. There is a bend 117 between coupling device 92 and grip 94 such that coupling device 92 is oriented in a downward angle A (FIG. 18) between about 5 degrees and about 90 degrees, or more narrowly between about 10 degrees and about 45 degrees. Other angles are possible. Grip 94 includes a plurality of arc-shaped depressions 118 to prevent the hand of the user from slipping off of grip 94. Slot 120 is formed into coupling device 92 and is sized to receive lance 22. The width of slot 120 is the same as or slightly larger than the cross-sectional diameter of the rod body of lance 22. Depression or groove 122 is formed at the end of slot 120 and is configured to allow lance 22 to pivot within the end of slot 120. For example, lance 22 can be inserted into opening 124 while lance 22 is perpendicular to surface plane 126 of lance coupling device 92. When lance 22 reaches groove 122, lance 22 can be pivoted from its perpendicular orientation to angle B less than 90 degrees relative to surface plane 126. Groove 122 is configured such that pivoting is stopped when angle B reaches an angle between about 10 degrees to 80 degrees, or more narrowly between about 10 degrees and about 45 degrees. Other angles are possible.

After pivoting lance 22 within slot 120 to angle B, the rod body of lance 22 is separated from the bottom surface of grip 94. The space between lance 22 and grip 94 is due to bend angle A, the distance of groove 122 from bend 117, and pivot angle B. When a user squeezes grip 94 and lance 22 together, surfaces of groove 122 and/or slot 120 press against lance 22, which engages handle 26B and lance 22 together. Friction between lance coupling device 92 and lance 22 prevents lance 22 from slipping relative to handle 26B when the user squeezes grip 94 and lance 22 together. In some embodiments, gripping features 35 of lance 22 prevents lance 22 from slipping relative to handle 26B.

In some embodiments angle B is greater than or equal to angle A to help ensure that the rod body of lance 22 remains separated from the bottom surface of grip 94.

Handle 26B (FIGS. 17-19) can be used in place of handle 26 (FIGS. 9A and 9B) or used in conjunction with handle 26 in the exemplary surgical tunneling methods described above. In some embodiments, the method includes the user manually holding gripping features 35 of the rod body of lance 22 to help maneuver, pull, and/or push lance 22.

The outer surface of gripping features 35 forms a hexagonal cross-section which prevents lance 22 from rotating about axis 108 relative to handle 26 and 26B, which allows the user to steer lance 22 through a desired tunnel path. The inner surface of tube 96 (FIG. 9B) of handle 26 forms a corresponding hexagonal cross-section and is configured to receive, engage, and prevent axial rotation of gripping feature 35 within tube 96. The bottom surface of engagement end 92 (FIG. 17) of handle 26B is configured to engage a flat surface of gripping feature 35 and prevent axial rotation of gripping feature 35. Other shapes, such has square and triangular, for the cross-section of gripping feature 35 can be implemented to prevent axial rotation relative to handle 26 and 26B.

In some embodiments, a surgical implantation kit includes cable adapter 24, cable 14, and optionally an operative device which, for example, can be a ventricular assist device, a controller for a ventricular assist device, or other medical device. In other embodiments, the surgical implantation kit further includes lance 22 and handle 26 or 26B, both of which lance and handle can be re-sterilized and reused to perform a tunneling procedure on another patient.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A surgical tunneler system for a ventricular assist device, the system comprising:
    a lance comprising a tapered tip and a rod body, the rod body having an axial length, the tapered tip having a point, a wide segment adjacent the point, and a narrow segment adjacent the wide segment, the narrow segment being narrower than the wide segment, the point and the wide segment forming a forward taper configured to allow the lance to be pushed through tissue in a first direction, the wide segment and the narrow segment forming a rearward taper configured to allow the lance to be pulled through the tissue in a second direction opposite the first direction;
    a handle comprising a coupling device, a slot formed through the coupling device, the slot sized to receive the rod body while the tapered tip is outside of the slot, the slot configured to engage and disengage the lance at multiple locations along the axial length of the rod body, the handle comprising a bend between the coupling device and a grip, the grip comprising a first end connected to the coupling device at the bend and a free end opposite the first end; and
    a depression formed at an end of the slot, the depression configured to allow the rod body to pivot within the end of the slot while the tapered tip is outside of the slot.

2. The system of claim 1, wherein the rod body has a cross-sectional diameter, and the slot has a width that is the same as or larger than the cross-sectional diameter of the rod body.

3. The system of claim 1, wherein the depression is configured to allow the rod body to pivot, within the end of the slot, from a first angle relative to a surface of the coupling device to a second angle relative to the surface of the coupling device, and the depression stops the rod body from pivoting when the rod body reaches the second angle.

4. The system of claim 3, wherein the first angle is 90 degrees from the surface of the coupling device, and the second angle is less than 90 degrees from the surface of the coupling device.

5. The system of claim 4, wherein the second angle is from 10 degrees to 80 degrees from the surface of the coupling device.

6. The system of claim 5, wherein the second angle is from 10 degrees to 45 degrees from the surface of the coupling device.

7. The system of claim 3, wherein the bend forms a bend angle between the grip and the surface of the coupling device.

8. The system of claim 7, wherein when the rod body reaches the second angle, the tapered tip is in front of the coupling device, a portion of the rod body is behind the coupling device and below the grip at a position spaced apart from a bottom surface of the grip to allow a user to squeeze the grip and the portion of the rod body together.

9. The system of claim 7, wherein the bend angle is from 5 degrees to 90 degrees from the surface of the coupling device.

10. The system of claim 9, wherein the bend angle is from 10 degrees to 45 degrees from the surface of the coupling device.

11. The system of claim 1, further comprising a cable adapter, the cable adapter comprising a lance connection portion and a cable connection portion, the lance connection portion configured to receive the tapered tip.

12. The system of claim 11, wherein the cable connection portion is configured to receive an electrical cable for transmitting control signals to a ventricular assist device.

13. The system of claim 11, further comprising an electrical cable for transmitting control signals to a ventricular assist device, and the cable connection portion is configured to receive the electrical cable.

14. A surgical tunneler system for a ventricular assist device, the system comprising:
    a lance comprising a tapered tip and a rod body, the rod body having an axial length, the tapered tip having a point, a wide segment adjacent the point, and a narrow segment adjacent the wide segment, the narrow segment being narrower than the wide segment, the point and the wide segment forming a forward taper configured to allow the lance to be pushed through tissue in a first direction, the wide segment and the narrow segment forming a rearward taper configured to allow the lance to be pulled through the tissue in a second direction opposite the first direction; and
    a handle comprising a coupling device, a slot formed through the coupling device, the slot sized to receive the rod body while the tapered tip is outside of the slot, the slot configured to engage and disengage the lance at multiple locations along the axial length of the rod body, the handle comprising a bend between the coupling device and a grip, the grip comprising a first end connected to the coupling device at the bend and a free end opposite the first end;

wherein a portion of the rod body is behind the coupling device and below the grip at a position spaced apart from a bottom surface of the grip to allow a user to squeeze the grip and the portion of the rod body together.

* * * * *